US006541472B1

(12) United States Patent
Pevear et al.

(10) Patent No.: US 6,541,472 B1
(45) Date of Patent: Apr. 1, 2003

(54) COMPOUNDS, COMPOSITIONS AND METHODS FOR PREVENTING AND TREATING PESTIVIRUS INFECTION AND ASSOCIATED DISEASES

(75) Inventors: Daniel C. Pevear, Harleysville, PA (US); Theodore J. Nitz, Pottstown, PA (US); Martin Seipel, Malvern, PA (US)

(73) Assignee: ViroPharma Incorporated, Exton, PA (US)

( * ) Notice: Subject to any disclaimer, the term of this patent is extended or adjusted under 35 U.S.C. 154(b) by 0 days.

(21) Appl. No.: 09/547,607

(22) Filed: Apr. 12, 2000

Related U.S. Application Data

(63) Continuation of application No. 09/136,818, filed on Aug. 20, 1998, now abandoned, which is a continuation-in-part of application No. 08/803,675, filed on Feb. 21, 1997, now Pat. No. 5,830,894.

(51) Int. Cl.[7] .................. C07D 487/04; A61K 31/53
(52) U.S. Cl. .................. 514/243; 514/217.05; 544/184; 540/599
(58) Field of Search .................. 514/243, 217.05; 544/184; 540/599

(56) References Cited

U.S. PATENT DOCUMENTS

| | | | |
|---|---|---|---|
| 3,312,699 A | 4/1967 | Gladych et al. | 544/184 |
| 3,452,013 A | 6/1969 | Gladych et al. | 544/184 |
| 3,466,281 A | 9/1969 | Gladych et al. | 544/184 |
| 3,466,282 A | 9/1969 | Gladych et al. | 544/184 |
| 3,467,657 A | 9/1969 | Gladych et al. | 544/184 |
| 3,493,569 A | 2/1970 | Gladych et al. | 544/184 |
| 3,493,571 A | 2/1970 | Gladych et al. | 544/184 |
| 3,637,687 A | 1/1972 | Chow | 544/184 |
| 3,752,891 A | 8/1973 | Kaminsky | 424/249 |
| 5,830,894 A | * 11/1998 | Pevear et al. | 514/243 |

FOREIGN PATENT DOCUMENTS

| | | |
|---|---|---|
| GB | 1168290 | 10/1969 |
| RU | 1825794 | 7/1993 |
| RU | 1786803 | 7/1994 |
| ZA | 68 04 428 | 11/1968 |

OTHER PUBLICATIONS

Database CAPLUS on STN, Chemical Abstract, vol. 126, No. 312280, Tomchin et al., "3–(2–(4–Methyl)piperzinoethylthio)–1,2,4–triazino[5,6–b]indole trihydrochloride accelerating recovery process after prolonged stress," abstract, Izobreteniya, vol. 27, page. Sep. 27, 1996.*
Database CAPLUS on STN, Chemical Abstract, vol. 122, No. 333427, Mohan et al., "Condensed bridgehead nitrogen heterocyclic systems," Indian J. Chem., Sect. B: Org. Chem., vol. 34B, No. 2, pages 125–128. 1995.*
Database CAPLUS on STN, Chemical Abstract, vol. 126, No. 325546, Tomchin et al., "3–(2–Dimethylamino)ethylamino–1,2,4–triazino[5,6–b]indole dihydrochloride improving resistance of organism against hypoxia," abstract, Izobreteniya, vol. 26, p. 241. Sep. 10, 1996.*
Jain et al., "Heterocyclic Systems Containing Bridgehead Nitrogen Atom. XLII"; Annales de la Societe Scientifique de Bruxelles, T. 96, I, pp. 59–67 (1982).
Tomchin et al., Chemical Abstract, vol. 126, No. 338864y, abstract Izobreteniya, vol. 25, pp. 244–245 (1996).
Turzhova et al., Chemical Abstract, vol. 126, No. 338866a, abstract Izobreteniya, vol. 25, p. 244 (1996).
Tomchin et al., Chemical Abstract, vol. 126, No. 338867b, abstract Izobreteniya, vol. 25, p. 244 (1996).
Tomchin et al., Chemical Abstract, vol. 126, No. 338868c, abstract Izobreteniya, vol. 25, p. 244 (1996).
Turzhova et al., Chemical Abstract, vol. 126, No. 338869d, abstract Izobreteniya, vol. 25, p. 244 (1996).
Tomchin et al, Chemical Abstract, vol. 126, No. 338870x, abstract Izobreteniya, vol. 25, p. 244 (1996).
Tomchin et al., Chemical Abstract, vol. 126, No. 338871y, abstract Izobreteniya, vol. 25, p. 243 (1996).
Tomchin et al., Chemical Abstract, vol. 126, No. 338875c, abstract Izobreteniya, vol. 25, p. 246 (1996).
Tomchin et al., Chemical Abstract, vol. 126, No. 338867d, abstract Izobreteniya, vol. 25, p. 246 (1996).
Tomchin et al., Chemical Abstract, vol. 126, No. 338877e, abstract Izobreteniya, vol. 25, pp. 245–246 (1996).
Tomchin et al., Chemical Abstract, vol. 126, No. 338878f, abstract Izobreteniya, vol. 25, p. 245 (1996).
Tomchin et al., Chemical Abstract, vol. 126, No. 312290h, abstract Izobreteniya, vol. 25, p. 243 (1996).
Tomchin et al., Chemical Abstract, vol. 126, No. 312292k, abstract Izobreteniya, vol. 25, p. 243 (1996).
Tomchin et al., Chemical Abstract, vol. 126, No. 312293m, abstract Izobreteniya, vol. 25, pp. 242–243 (1996).
Tomchin et al., Chemical Abstract, vol. 123, No. 276058n, abstract Izobreteniya, vol. 14, p. 187 (1994).
M. Giangaspero et al., Arch. Virol. Suppl., 7:53–62 (1993).
M. Giangaspero et al., Int. J. Std. Aids, 4(5): 300–302 (1993).
R. Yolken et al., Lancet, 1(8637): 517–20 (1989).
C.R. Wilks et al., Lancet, 1: (8629): 107 (1989).
M. Giangaspero et al., Lancet, 2: 110 (1988).
B.J. Potts et al., Lancet, 1(8539): 972–973 (1987).
J. Gladych et al., J. Medicinal Chemistry, 15: 277–281 (1972).

(List continued on next page.)

*Primary Examiner*—John M. Ford
(74) *Attorney, Agent, or Firm*—Dann Dorfman Herrell and Skillman, P.C.

(57) ABSTRACT

Triazinoindole derivatives are useful in the prophylaxis and treatment of pestivirus infections and diseases associated with pestivirus infections.

14 Claims, No Drawings

OTHER PUBLICATIONS

M.S. Collett et al., Virology, 165: 191–199 (1988).
Pauwels et al., J. Virol. Methods, 20: 309–321 (1988).
J. Boyle et al., Annals of the NY Academy of Science, 173: 477–491 (1970).
J.M.Z. Gladych, Nature, 221: 286–287 (1969).
M. Younes et al., Arch. Pharm. (Weinheim), 320: 1196–1202 (1987).
K. Wegner et al., Arch Pharm. (Weinheim), 320: 108–114 (1987).
K. Joshi et al., J. Indian Chem. Soc., LVII: 1176–1180 (1980).
V. Ram, Arch. Pharm. (Weinheim), 313: 108–113 (1980).
A. Sengupta et al., J. Indian Chem. Soc., LXII: 165–168 (1985).
K.C. Joshi et al., Journal f. prakt. Chemie. Band, 322: 314–320 (1980).
M.S. Collett, J. Gen. Virol., 69: 2637–2643 (1988).
M.S. Collett, Comp. Immun. Microbiol. Infect. Dis., 15: 145–154 (1992).
Tomchin et al., Chemical Abstract, vol. 123, No. 340195, abstract Izobreteniya, vol. 25, pp. 31–32 (1993).
Tomchin et al., Khim.–Farm. Zh., vol. 32, No. 1, pp. 22–26 (1998).
Tomchin et al., Chemical Abstract, vol. 126, No. 312289, abstract Izobreteniya, vol. 25, p. 243 (1996).
Tomchin et al., Chemical Abstract, vol. 126, No. 312263, abstract, Izobreteniya, vol. 25, p. 242 (1996).
Tomchin et al. Chemical Abstract, vol. 126, No. 312281, abstract, Izobreteniya (1996).
Tomchin et al., Chemical Abstract, vol. 126, No. 344463, abstract, Izobreteniya, vol. 27 (Sep. 27, 1996).
Mohan et al., Chemical Abstract, vol. 122, No. 333427, abstract, Indian J. Chem., Sect. B: Org. Chem., vol. 34B, No. 2, pp. 125–128 (1995).
Tomchin et al., Chemical Abstract, vol. 126, No. 361432, abstract, Izobreteniya, vol. 26, p. 241 (Sep. 10, 1996).
Pauwels et al., *J. Virol. Methods*, 20: 309–321 (1988).
J. Boyle et al., *Annals of the NY Academy of Science*, 173: 477–491 (1970).
J.M.Z. Gladych, *Nature*, 221: 286–287 (1969).
M. Younes et al., *Arch. Pharm.* (*Weinheim*), 320: 1196–1202 (1987).
K. Wegner et al., *Arch. Pharm.* (*Weinheim*), 320: 108–114 (1987).
K. Joshi et al., *J. Indian Chem. Soc.,* LVII: 1176–1180 (1980).
V. Ram, *Arch. Pharm.* (*Weinheim*), 313: 108–113 (1980).
A. Sengupta et al., *J. Indian Chem. Soc.,* LXII: 165–168 (1985).

* cited by examiner

COMPOUNDS, COMPOSITIONS AND METHODS FOR PREVENTING AND TREATING PESTIVIRUS INFECTION AND ASSOCIATED DISEASES

CROSS REFERENCE TO RELATED APPLICATIONS

The present application is a continuation of U.S. patent application Ser. No. 09/136,818, filed Aug. 20, 1998, now abandoned, which is a continuation-in-part of U.S. patent application Ser. No. 08/803,675, filed Feb. 21, 1997, now U.S. Pat. No. 5,830,894.

FIELD OF THE INVENTION

The present invention relates to compounds and compositions for preventing and treating virus infections and the diseases associated therewith, particularly those infections and associated diseases caused by viruses in the Flaviviridae family, especially the pestiviruses.

BACKGROUND OF THE INVENTION

The Flaviviridae family of viruses is composed of three genera: pestivirus, flavivirus and hepacivirus (hepatitis C virus).

The pestivirus genus consists of the prototypic member bovine viral diarrhea virus (BVDV), classical swine fever virus (CSFV, also called hog cholera virus) and border disease virus (BDV) of sheep. Human pestiviruses have not been as extensively characterized as the animal pestiviruses. However, serological surveys indicate considerable pestivirus exposure in humans. Pestivirus infections in man have been implicated in several diseases including, but not likely limited to, congenital brain injury, infantile gastroenteritis and chronic diarrhea in human immunodeficiency virus (HIV) positive patients. M. Giangaspero et al., Arch. Virol. Suppl., 7: 53–62 (1993); M. Giangaspero et al., Int. J. STD. AIDS, 4(5): 300–302 (1993); R. Yolken et al., Lancet, 1(8637): 517–20 (1989); C. R. Wilks et al., Lancet, 1(8629): 107 (1989); M. Giangaspero et al., Lancet, 2: 110 (1988); B. J. Potts et al., Lancet, 1(8539): 972–973 (1987).

Pestivirus infections of domesticated livestock (cattle, pigs, and sheep) cause significant economic losses worldwide. BVDV is ubiquitous and causes a range of clinical manifestations including abortion, teratogenesis, respiratory problems, chronic wasting disease, immune system dysfunction and predisposition to secondary viral and bacterial infections. Certain BVDV strains are capable of causing an acute fatal disease, with mortality rates of 17% to 32%. BVDV is also able to establish persistent infections in fetuses infected before 150 days of gestation. When born, these persistently infected (PI) animals are immunotolerant to the infecting BVDV strain and remain viremic throughout life. PI animals constitute 1% to 2% of the cattle population in the United States and serve as virus reservoirs and continuous sources for virus spread in herds. PI animals may also succumb to fatal mucosal disease upon superinfection with closely related, but distinct, BVDV virus strains. CSFV, while eradicated from the United States and Canada, causes widespread disease in Europe and elsewhere in the world.

Flaviviruses and hepaciviruses represent important pathogens of man and are also prevalent throughout the world. There are 38 flaviviruses associated with human disease, including the dengue fever viruses, yellow fever virus and Japanese encephalitis virus. Flaviviruses cause a range of acute febrile illnesses and encephalitic and hemorrhagic diseases. Hepaciviruses currently infect approximately 1 of the world population and cause persistent infections leading to chronic liver disease, cirrhosis, hepatocellular carcinoma and liver failure.

Currently, there are no antiviral pharmaceutical drugs to prevent or treat pestivirus or flavivirus infections. For hepacivirus (hepatitis C virus) infections, interferon alfa (IFN) is currently the only approved drug in the United States. While IFN treatment has been reported to improve symptoms in 20% to 40% of patients, the remainder do not respond favorably to IFN treatment. For patients who do respond, a sustained improvement of liver function reportedly is seen in only 10% to 20% of patients; the majority of patients relapse upon cessation of IFN treatment. Thus, while IFN has been shown to have some utility in treating hepatitis C, its effectiveness is limited and its cure rate is low.

SUMMARY OF THE INVENTION

In accordance with one aspect, the present invention provides a compound and composition for preventing and treating pestivirus infection and for preventing and treating diseases associated with pestivirus infection in mammalian hosts. The compounds of the invention have the following structure:

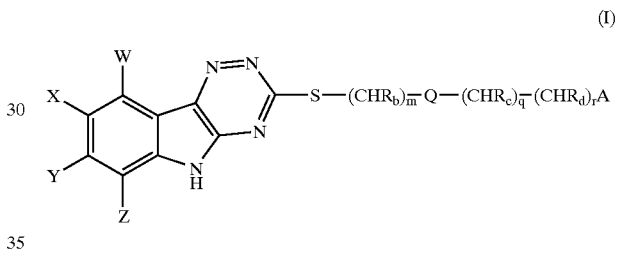

(I)

in which A represents a substituent selected from the group consisting of:

(a) $NR_1R_2$ wherein $R_1$ and $R_2$ are radicals independently selected from the group consisting of H, straight or branched chain alkyl groups ($C_1$–$C_6$), substituted or unsubstituted aryl groups, substituted or unsubstituted aralkyl groups in which the alkyl group is $C_1$–$C_6$, alkoxy groups ($C_1$–$C_6$), acyl groups ($C_1$–$C_7$), substituted or unsubstituted carbalkoxy groups ($C_1$–$C_8$ alkoxy), or $R_1$ and $R_2$, together with the nitrogen atom to which they are attached, represent a substituted or unsubstituted heterocyclic ring selected from the group consisting of benzopyridazine, indole, benzotriazole, hexamethyleneimine, imidazole, isoxazole, morpholine, phthalimide, piperidine, piperazine and pyrrolidine;

(b) a substituted or unsubstituted heterocyclic group selected from the group consisting of pyridine, benzimidazole, benzodioxane, benzofurazan, indole, benzothiophene, coumarin, furan, hexamethyleneimine, isoxazole, oxadiazole, piperazine, piperidine, pyridine, pyrimidine, pyrrolidine, quinoline, quinuclidene, tetrahydropyran and thiazole;

(c) a substituted or unsubstituted phenyl group; and (d) $OR_3$, wherein $R_3$ represents a radical selected from the group consisting of H, a straight or branched chain alkyl ($C_1$–$C_6$) group, a substituted or unsubstituted phenyl group a substituted or unsubstituted phenylalkyl group wherein the alkyl group is $C_1$–$C_6$, or a substituted or unsubstituted tetrahydropyran; Q represents a linking moiety selected from the group consisting of —[(A')$_n$—(CO)]$_p$—, —S—, —(SO)—, —(SO$_2$)— or a valence bond, A' being —NR$_a$— or —O— and R$_a$ being H or alkyl (C$_1$–C$_6$); R$_b$, R$_c$ and R$_d$ independently represent H, alkyl (C$_1$–C$_4$), substituted or unsubstituted phenyl or COOR, R being hydrogen or alkyl (C$_1$–C$_6$); m is an integer from 0 to 6; n and p independently represent 0 or 1; and q and r are independently integers from 0 to 4; said phenyl, aryl, aralkyl, carbalkoxy and heterocyclic substituents and the W, X, Y and Z substituents being selected from the group consisting of H, alkyl (C$_1$–C$_6$), substituted or unsubstituted aryl (C$_6$–C$_{15}$), substituted or unsubstituted aralkyl (C$_7$–C$_{15}$), halogen, CF$_3$, CN, O-alkyl (C$_1$–C$_6$), acyloxy (C$_1$–C$_6$ acyl), S-alkyl (C$_1$–C$_6$), SO-alkyl (C$_1$–C$_6$), SO$_2$-alkyl (C$_1$–C$_6$), NH$_2$SO$_2$, NO$_2$, NH$_2$, NHR', NR'R", alkyl COOR', COOR', alkyl CONR'R", CONR'R",

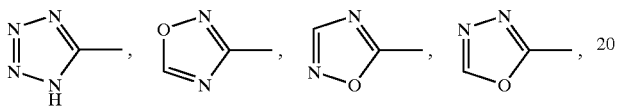

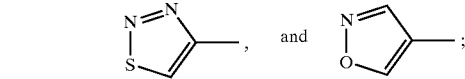

R' and R" being independently selected from the group consisting of hydrogen or alkyl (C$_1$–C$_6$), and the isomers and pharmaceutically acceptable salts of said compound.

DETAILED DESCRIPTION OF THE INVENTION

The compounds of the invention can be conveniently prepared from known starting materials according to the general synthetic scheme illustrated below. Specific embodiments of anti-pestivirus compounds within the scope of the invention are exemplified below.

In the general synthetic scheme, thiosemicarbazide is reacted with isatin to form 5H-1,2,4-triazino[5,6-b]indole-3(2H)-thione. This product is alkylated with an appropriate halo-derivative to provide the sulfur-substituent desired in the final product.

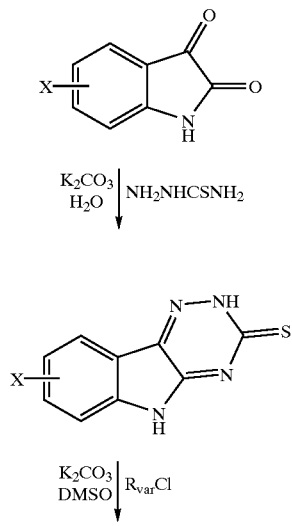

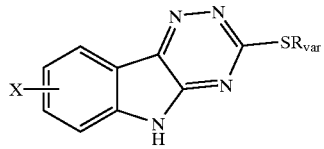

R$_{var}$ signifies any of the various sulfur substituents mentioned above with reference to the compounds of Formula I.

In vitro studies have been performed demonstrating the usefulness of compounds described herein as antiviral agents against pestiviruses. Antiviral activity was measured on the basis of activity against bovine viral diarrhea virus (BVDV) in a cell culture assay. The specificity of antiviral activity toward pestiviruses was also demonstrated in cell culture. Animal safety and bioavailability studies were also performed. The biological studies of the antiviral activity of the compounds of the invention are also described in the examples that follow.

Compounds with particular utility, including isomeric forms, have the formula:

(II)

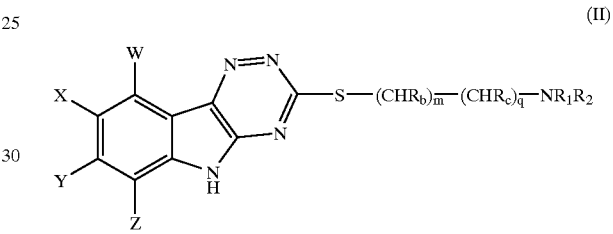

in which R$_1$ and R$_2$ are the same or different straight or branched chain alkyl groups (C$_1$–C$_6$), or R$_1$ and R$_2$, together with the nitrogen atom to which they are attached form a substituted or unsubstituted heterocyclic ring having from 5 to 9 ring atoms, with nitrogen being the only heteroatom in the ring, the heterocyclic ring substituents being selected from the group consisting of hydrogen, alkyl (C$_1$–C$_6$), halogen, CF$_3$, CN and O-alkyl (C$_1$–C$_6$), m is an integer from 1–6, and R$_b$, R$_c$, W, X, Y, Z, b, c, and q are as previously defined with reference to Formula I, and the pharmaceutically acceptable salts of such compounds.

Particularly preferred are the following compounds:
3-[(2-pyridylmethyl)thio]-5H-1,2,4-triazino[5,6-b]indole, 3-[2-(4-morpholino)ethylthio]-5H-1,2,4-triazino[5,6-b]indole, 3-[4-((6,7-dimethoxy-2-oxo-2H-1-benzopyranyl)methyl)thio]-5H-1,2,4-triazino[5,6-b]indole, 3-[(2-(4-(1-ethylpiperidinyl)ethyl)thio]-5H-1,2,4-triazino[5,6-b]indole, 3-[(2-((4-benzodioxanyl))methyl)thio]-5H-1,2,4-triazino[5,6-b]indole, 3-[(4-(2,6-dichloropyridyl)methyl)thio]-5H-1,2,4-triazino[5,6-b]indole, 3-[4-(((2-tetrahydro-2H-pyranyl)oxy)butyl)thio]-5H-1,2,4-triazino[5,6-b]indole, and the isomers and pharmaceutically acceptable salts of those compounds.

As previously noted, the compounds of formula I above and their pharmaceutically acceptable salts exhibit antiviral activity against pestivirus. The compounds of the invention are particularly useful in treating and preventing pestivirus infections (and diseases) in the livestock industry, and may be used to treat cattle, swine and sheep, or other animals susceptible to pestivirus infection.

Compounds of the invention are similarly useful in treating and preventing pestivirus infections in humans. In addition, the compounds of the invention may further have application in the treatment and prevention of infections and diseases of mammalian species by viruses related to the pestiviruses, in particular, the flaviviruses and hepaciviruses.

Compounds described herein are also useful for the treatment of biological material that is susceptible to infection by, or infected or contaminated with a pestivirus. These compounds are especially useful for preventing or resolving pestiviral infections in cell cultures, tissue cultures and other in vitro applications. For example, inclusion of compounds of the invention as a supplement in cell or tissue culture growth media and cell or tissue culture components will prevent pestiviral infections of cultures not previously infected with pestiviruses. Compounds described above may also be used to eliminate pestiviruses from cultures or other materials infected with pestiviruses (e.g., blood), after a suitable treatment period, under any number of treatment conditions as determined by the skilled artisan. This aspect of the invention may be used to advantage in treating cell cultures comprising bovine serum or other mammalian serum. For example, bovine serum can be contaminated with pestiviruses, including BVDV, classical swine fever virus (hog cholera virus) and border disease virus, and the compounds and compositions of the invention can be used to inhibit the growth of those viruses in applications wherein bovine serum is used.

The utility of such in vitro applications of the compounds of the invention will be broad in scope and will include, but not be limited to, use of the compounds of the invention in research and diagnostic laboratories and use in the manufacture of diagnostic, vaccine and therapeutic products for veterinary and human use.

The compounds of the invention can form useful salts with inorganic and organic acids, including, for example, hydrochloric acid, hydrobromic acid and methane sulfonic acid.

The pharmaceutically acceptable salts of the compounds of formula I are prepared following procedures which are familiar to those skilled in the art.

The antiviral pharmaceutical compositions of the present invention comprise one or more of the compounds of formula I, above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the antiviral compounds of the invention, such as by producing any undesirable biological effect or otherwise interacting in a deleterious manner with any other component(s) of the pharmaceutical composition, its use is contemplated to be within the scope of this invention.

In the pharmaceutical compositions of the invention, the active agent may be present in an amount of at least 0.5% and generally not more than 90% by weight, based on the total weight of the composition, including carrier medium and/or auxiliary agent(s), if any. Preferably, the proportion of active agent varies between 5–50% by weight of the composition.

Pharmaceutical organic or inorganic solid or liquid carrier media suitable for enteral or parenteral administration can be used to make up the composition. Gelatine, lactose, starch, magnesium stearate, talc, vegetable and animal fats and oils, gum, polyalkylene glycol, or other known carriers for medicaments may all be suitable as carrier media.

The compounds of the invention may be administered using any amount and any route of administration effective for attenuating infectivity of the pestivirus. Thus, the expression "amount effective to attenuate infectivity of pestivirus", as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like.

The anti-pestivirus compounds are preferably formulated in dosage unit form for ease of administration and uniformity of dosage. Dosage unit form as used herein refers to a physically discrete unit of antiviral agent appropriate for the patient to be treated. Each dosage should contain the quantity of active material calculated to produce the desired therapeutic effect either as such, or in association with the selected pharmaceutical carrier medium. Typically, the antiviral compounds of the invention will be administered in dosage units containing from about 0.1 mg to about 50 mg of the antiviral agent, with a range of about 1 mg to about 25 mg being preferred.

The compounds of the invention may be administered orally, parenterally, such as by intramuscular injection, intraperitoneal injection, aerosol, intravenous infusion or the like, depending on the nature and severity of the infection being treated. The compounds of the invention may be administered orally or parenterally at dosage levels of about 0.01 to about 1000 mg/kg, and preferably from about 1 to about 100 mg/kg of subject body weight per day, one or more times a day, to obtain the desired therapeutic effect.

Although the triazinoindole derivatives described herein can be administered to any host which is susceptible to pestivirus infection, the compounds are intended for the treatment of mammalian hosts, and especially livestock and humans.

The compounds of the invention will typically be administered from 1 to 4 times a day so as to deliver the above-mentioned daily dosage. However, the exact regimen for administration of the compounds and compositions described herein will necessarily be dependent on the needs of the individual host being treated, the type of treatment administered and the judgment of the attending veterinarian.

In view of the inhibitory effect on pestivirus replication in cell culture produced by the compounds used in the method of the invention, it is anticipated that these compounds will be useful not only for therapeutic treatment of pestivirus infection, but for pestivirus prophylaxis, as well.

The following examples are provided to describe the invention in further detail. These examples, which set forth a preferred mode presently contemplated for carrying out the invention, are intended to illustrate and not to limit the invention.

Example 1 illustrates the chemical synthesis of one of the compounds of the invention.

EXAMPLE 1

Preparation of 3-[((2-Dipropylamino)ethyl)thio]-5H-1,2,4-triazino[5,6-b]indole 5H-1,2,4-Triazino[5,6-b]indole-3(2H)-thione A mixture of 7.36 g (50.0 mmoles) of isatin, 250 ml of water, 5.01 g (55.0 mmoles) of thiosemicarbazide and 10.4 g (75.0 mmoles) of potassium carbonate was heated to reflux. After 30 minutes, a red solution resulted which was cooled to room temperature and filtered through celite. The pH was adjusted to 4.5 with glacial acetic acid and the resulting yellow solid was collected and washed with hot ethanol. After drying, 8.04 g of material was obtained. (*J. Medicinal Chemistry*, 15:277 (1972))

b. 3-[((2-Dipropylamino)ethyl)thio]-5H-1,2,4-triazino[5,6-b]indole

To a mixture of 222 mg (1.10 mmole) of 5H-1,2,4-triazino[5,6-b]indole-3(2H)-thione, 340 mg (2.5 mmole) of milled potassium carbonate and 2.5 ml of dry dimethylsulfoxide was added 200 mg (1.00 mmole) of dipropylaminoethylchloride. The mixture was stirred for 12 hours and then poured into 25 ml of water. The resultant solid was collected by filtration, washed with water and dried to provide 258 mg of a yellow solid, which analysis showed to be the title compound.

By appropriate selection of specific halo-derivatives to provide the desired sulfur substituent, other products within the scope of the invention can be prepared by analogous reactions. Particularly preferred are reactants having the structures given in the following table.

TABLE 1

| Example Number | S-substituent | Product |
| --- | --- | --- |
| 2 | *propyl-N(ethyl)₂ group* | *3-[(2-diethylamino)ethylthio]-5H-1,2,4-triazino[5,6-b]indole* |
| 3 | *propyl-N(isopropyl)₂ group* | *3-[(2-diisopropylamino)ethylthio]-5H-1,2,4-triazino[5,6-b]indole* |
| 4 | *isobutyl-N(methyl)₂ group* | *triazinoindole with methylpropyl-N(Me)₂ sulfide* |
| 5 | *ethyl-N(methyl)₂ group* | *3-[(2-dimethylamino)ethylthio]-5H-1,2,4-triazino[5,6-b]indole* |
| 6 | *propyl-pyrrolidine group* | *triazinoindole with ethyl-pyrrolidine sulfide* |
| 7 | *propyl-piperidine group* | *triazinoindole with ethyl-piperidine sulfide* |
| 8 | *butyl-piperidine group* | *triazinoindole with propyl-piperidine sulfide* |

TABLE 1-continued
| Example Number | S-substituent | Product |
|---|---|---|
| 9 | 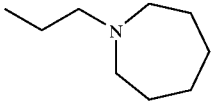 | 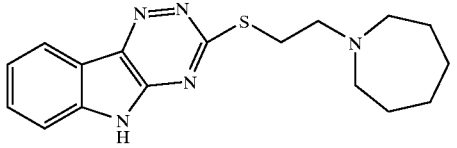 |
| 10 | 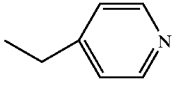 | 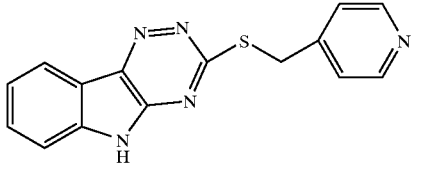 |
| 11 | 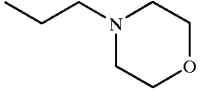 | 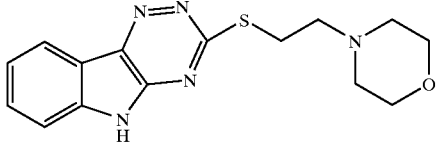 |
| 12 | 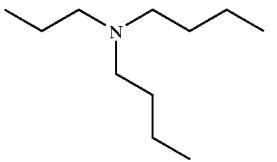 | 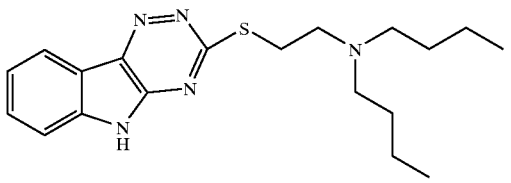 |
| 13 | 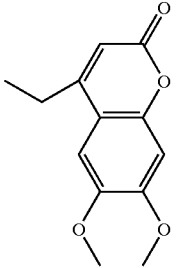 | 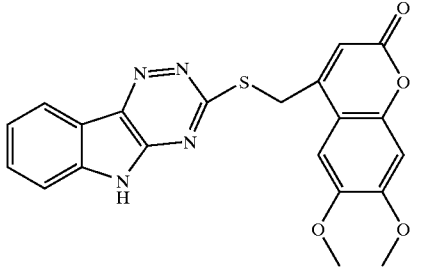 |
| 14 | 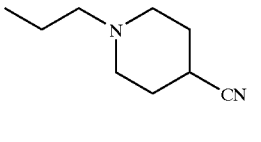 | 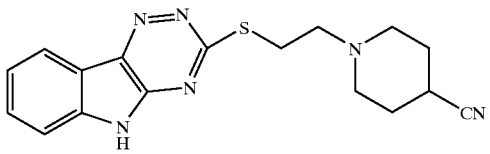 |
| 15 | 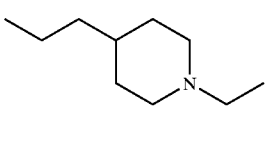 | 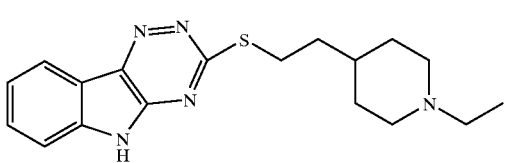 |
| 16 | 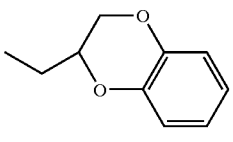 | 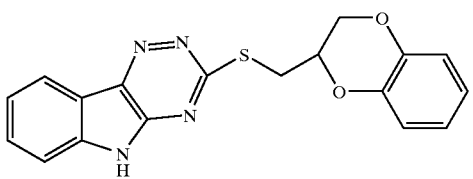 |

TABLE 1-continued

| Example Number | S-substituent | Product |
|---|---|---|
| 17 | 2,6-dichloro-4-ethylpyridine | 3-[(2,6-dichloropyridin-4-yl)methylthio]-5H-[1,2,4]triazino[5,6-b]indole |
| 18 | 4-(tetrahydropyran-2-yloxy)butyl | 3-[4-(tetrahydropyran-2-yloxy)butylthio]-5H-[1,2,4]triazino[5,6-b]indole |
| 19 | 2-(dipropylamino)ethyl | 3-[2-(dipropylamino)ethylthio]-8-methyl-5H-[1,2,4]triazino[5,6-b]indole |
| 20 | 2-(azepan-1-yl)ethyl | 3-[2-(azepan-1-yl)ethylthio]-8-methyl-5H-[1,2,4]triazino[5,6-b]indole |
| 21 | 2-(piperidin-1-yl)ethyl | 8-bromo-3-[2-(piperidin-1-yl)ethylthio]-5H-[1,2,4]triazino[5,6-b]indole |
| 22 | 2-(azepan-1-yl)ethyl | 8-bromo-3-[2-(azepan-1-yl)ethylthio]-5H-[1,2,4]triazino[5,6-b]indole |
| 23 | 2-(azepan-1-yl)ethyl | 3-[2-(azepan-1-yl)ethylthio]-8-fluoro-5H-[1,2,4]triazino[5,6-b]indole |
| 24 | 2-(piperidin-1-yl)ethyl | 8-methyl-3-[2-(piperidin-1-yl)ethylthio]-5H-[1,2,4]triazino[5,6-b]indole |

TABLE 1-continued

| Example Number | S-substituent | Product |
|---|---|---|
| 25 | | |
| 26 | | |
| 27 | | |

The compounds of the invention can be also conveniently prepared from known starting materials according to the alternate synthetic scheme illustrated below. The alternate synthetic scheme, which uses the appropriate alcohol to provide the desired sulfur substituent, may be used when the corresponding halo-derivative is not available. In the alternate synthesis, 5H-1,2,4-triazino[5,6-b]indole-3(2H)-thiol is reacted in the presence of diethyl azodicarboxylate to effect coupling of the alcohol reactant in forming the desired product. The oxygen resulting from the reaction is taken up by the oxygen scavenger, triphenylphosphene, to form triphenylphospene oxide.

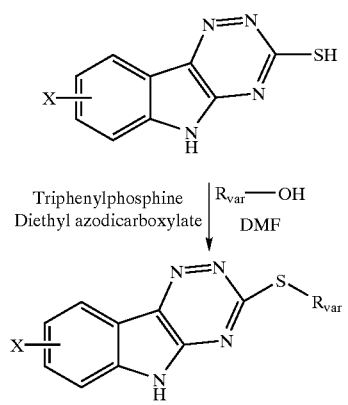

Example 28 illustrates the alternate synthetic method for the synthesis of the compound prepared in Example 1.

EXAMPLE 28

Alternate Preparation of 3-[((2-Dipropylamino)ethyl)thio]-5H-1,2,4-triazino[5,6-b]indole A solution of 0.45 ml (2.86 mmol) of diethylazodicarboxylate in 5 ml of dry dimethylformamide was added dropwise to a suspension of 506 mg (2.5 mmol) of 5H-1,2,4-triazino[5,6-b]indole-3-thiol, 20 ml of dry dimethylformamide, 721 mg (2.7 mmol) of triphenylphosphine and 399 mg (2.75 mmol) of 2-dipropylaminoethanol. After 30 minutes, complete solution had occurred. The solution was stirred for 12 hours at room temperature and then poured into 50 ml of water. The resulting solid was collected by filtration, washed with water, dissolved in 50 ml of ethyl acetate and transferred to a separatory funnel. The solution was extracted three times with 25 ml of 1N hydrochloric acid and water. The combined aqueous phases were filtered through celite and then made basic with 15% sodium hydroxide. The solid which separated was collected, washed with water and dried to yield 457 mg of a yellow solid, which analysis showed to be the title compound.

Example 29 illustrates the efficacy of the compounds of the invention in inhibiting the viral replication of BVDV in cell culture.

EXAMPLE 29

Cell Culture Assay for Inhibition of Pestivirus Replication

The replication of many viruses may be quantitatively assessed in the laboratory in various cell or tissue culture systems. Such in vitro culture methodologies are available and useable by those trained in the art for the propagation and quantitative measurement of the replication of several pestiviruses and flaviviruses. The following procedure was used for the in vitro quantitative measure of BVDV replication.

Using the procedure described in this example, compounds of the invention were evaluated for their ability to inhibit the replication of the virus in cell culture. By adding compounds at various concentrations to the culture medium, a dose response effect of the compound on virus replication can be determined. A useful quantitative measure of the inhibition of BVDV replication in this assay is the concentration of the compound at which virus replication in cell culture is inhibited by 50% in comparison to that observed in the absence of the compound (50% Inhibitory Concentration, $IC_{50}$).

Anti-pestivirus compounds of the invention were screened for antiviral activity against BVDV on Madin Darby bovine kidney (MDBK) cells in a cell culture assay. Standard 96-well culture plates were seeded with 1 to $2\times10^4$ MDBK cells in 200 uL of Dulbeccos-modified Eagle's medium (DMEM) supplemented with 5% horse serum so as to obtain a monolayer of cells at 60% confluence. Six hours later, the medium was removed and the cell monolayers in each well were infected with 150 uL solution of BVDV (strain NADL) (M.S. Collett et al., *Virology* 165:191–199 (1988)) in DMEM supplemented with 2% horse serum previously titrated to yield 85–100% destruction (cytopathic effect) of the cell monolayer 36–40 hours after infection.

To determine the $IC_{50}$ values of compounds tested in this experiment, ten serial 2-fold dilutions of test compounds were prepared in DMSO solvent at a compound concentration 200 times that desired for the highest final test concentration. The test compound-DMSO solutions were diluted 50-fold into DMEM containing 2% horse serum. Fifty uL of this dilution was added to the 150 uL volume present in the wells of the virus-infected plate, yielding a final DMSO concentration in each well of 0.5%. Virus control (VC; no test compound) and cell culture control (CC; no virus and no test compound) wells were included on each 96-well plate. Assay points were conducted in replicate, usually in quadruplicate. Plates were then incubated at 37° C. in a humidified atmosphere containing 2.5% carbon dioxide for 36–40 hours. At the end of the incubation period, 100 uL of a 5% solution of glutaraldehyde in water was added to each well and the wells were incubated at room temperature for 1 hour. The fixative was removed, and the cells S were stained with a 0.1% solution of crystal violet in water for 15–30 minutes. After rinsing and drying the plates, the optical density of the wells was measured at 570 nm ($OD_{570}$).

To determine $IC_{50}$ values for the test compounds, the mean value of the $OD_{570}$ readings of the virus control wells (VC) on a plate was subtracted from the $OD_{570}$ readings of all wells on that plate. The $IC_{50}$ values were then calculated according to the following formula:

$$IC_{50} = \left[\left(\frac{(Y-B)}{(A-B)}\right) \times (H-L) + L\right]$$

where Y represents the mean $OD_{570}$ reading of the cell control wells (CC) divided by 2; B represents the mean $OD_{570}$ reading of wells of the compound dilution nearest to and below Y; A represents the mean $OD_{570}$ reading of wells of the compound dilution nearest to and above Y; L represents the compound concentration at B; and H represents the compound concentration at A.

The results of the cell culture assay for inhibition of BVDV replication for compounds of the invention are given in Table 2.

TABLE 2

| Example | $IC_{50}$ ($\mu$M) |
| --- | --- |
| 1 | 0.006 |
| 2 | 0.3 |
| 3 | 3.1 |
| 4 | 3.7 |
| 5 | 5.5 |
| 6 | 0.5 |
| 7 | 0.06 |
| 8 | 4.4 |
| 9 | 0.03 |

TABLE 2-continued

| Example | $IC_{50}$ ($\mu$M) |
| --- | --- |
| 10 | 4.0 |
| 11 | 1.2 |
| 12 | 0.01 |
| 13 | 1.7 |
| 14 | 1.8 |
| 15 | >3.0 |
| 16 | 2.5 |
| 17 | 1.4 |
| 18 | >3.0 |
| 19 | 0.002 |
| 20 | 0.007 |
| 21 | 0.036 |
| 22 | 0.042 |
| 23 | 0.014 |
| 24 | 0.013 |
| 25 | 2.0 |
| 26 | 0.010 |
| 27 | 0.021 |

The low concentrations of drug compounds required to achieve 50% inhibition of viral replication in cell culture indicate that the drug compounds of the invention are effective at inhibiting the pestivirus replication process.

Example 30 illustrates the specificity of inhibition of pestivirus replication by three compounds of the invention.

EXAMPLE 30

Assay for Specificity of Inhibitors of Pestivirus Replication

For inhibitors of virus replication to be therapeutically useful, they must show clear specificity in their action. That is to say, the inhibitors should not be so non-specific that they inhibit unrelated viruses or inhibit activities essential to the health of the cell.

To demonstrate the specificity and selectivity of the compounds claimed herein, compounds of the invention were evaluated for their ability to inhibit the cell culture replication of several viruses unrelated to pestiviruses, including a paramyxovirus (respiratory syncytial virus), an orthomyxovirus (influenza virus), a picornavirus (coxsackie B3 virus), and a herpesvirus (herpes simplex virus II). The results of the specificity assay using compounds prepared in Examples 1, 7 and 9 are given in Table 3.

TABLE 3

| | $IC_{50}$ ($\mu$M) Compound according to Example: | | |
| --- | --- | --- | --- |
| Virus | 1 | 7 | 9 |
| BVDV | 0.006 | 0.06 | 0.03 |
| Respiratory syncytial virus | >50 | >50 | >50 |
| Influenza A virus | >50 | >50 | >50 |
| Coxsackie B3 virus | >50 | >50 | >50 |
| Herpes simplex virus type 2 | >50 | >50 | >50 |

A low concentration of the compounds prepared in Examples 1, 7 and 9 was sufficient to inhibit BVDV replication; however, even at much higher concentrations of these compounds, the unrelated viruses tested in the assay were not inhibited. The results in Table 3 show that the compounds prepared in Examples 1, 7 and 9 selectively inhibited the pestivirus and showed no activity against the unrelated viruses at the doses tested.

Example 31 demonstrates that the compounds of the invention are not toxic or detrimental to the health of normal cells by measuring cell viability.

EXAMPLE 31

MTT Cytotoxicity Assay

To demonstrate that the compounds of the invention are not toxic or detrimental to the health of normal cells, compounds of the invention were evaluated in an in vitro cytotoxicity assay. One useful assay for determining the cytotoxic effects of compounds on the growth of cells is a tetrazolium-based calorimetric method (Pauwels et al. *J. Virol. Methods* 20: 309–321 (1988)). This assay measures cell viability, and therefore cytotoxicity, by quantitatively detecting the in situ reduction of 3-(4,5-dimethylthiazol-2-yl)-2,5-diphenyltetrazolium bromide (MTT) by viable cells. Cells are seeded in 96-well plates in DMEM containing 2% horse serum at a density of $4 \times 10^3$ cells per well. After incubation for 4 hours at 37° C. and 5% $CO_2$, 2-fold serial dilutions of compound in 1% DMSO (or solvent alone) are added to quadruplicate wells and the plates are incubated for an additional 68 hours at 37° C. and 5% $CO_2$, which is equivalent to 3 to 4 cell doublings. The culture medium is removed, and the cells are treated with 1 mg/ml of MTT in phosphate-buffered saline, pH 7.2 for 4 hours at 37° C. and 5% $CO_2$. After removal of the unreduced MTT, the reduced blue formazan crystals produced by the viable cells are solubilized by the addition of 0.04N HCl in isopropanol. The absorbance at 570 nm ($A_{570}$) of each well is read using a suitable microplate reader. Cell viability is expressed as the percentage of optical density for compound-treated cells relative to the optical density of solvent alone-treated control wells. The highest compound concentration resulting in an optical density of $\geq 75\%$ of the control is represented as the cellular cytotoxicity value ($CC_{75}$). The results of the MTT cytotoxicity assay using compounds prepared in Examples 1, 7 and 9 are given in Table 4.

TABLE 4

| Compound | $CC_{75}$ ($\mu M$) | $IC_{50}$ ($\mu M$) | SI |
| --- | --- | --- | --- |
| Example 1 | 2 | 0.006 | 333 |
| Example 7 | 12.5 | 0.06 | 208 |
| Example 9 | 25 | 0.03 | 833 |

As shown in Table 4, the cellular cytotoxicity ($CC_{75}$) values are considerably higher than the antiviral ($IC_{50}$) values for these compounds. That result indicates that the compounds of the invention are highly selective and, at therapeutically effective doses, they do not detrimentally affect the health of normal cells. A measure of this selectivity is reflected by a high selective index value (SI), which is defined as $CC_{75}/IC_{50}$.

Examples 32 and 33 present the results of animal safety studies and bioavailability studies.

EXAMPLE 32

Animal Safety Studies

For inhibitors of pestivirus replication in cell culture to be useful for the prophylaxis and treatment of infections of pestiviral etiology in living beings, they must be safe in living beings. One useful measure of a compound's safety, known as the maximum tolerated dose (MTD), is defined as the highest dose of the compound that, when administered to a laboratory animal, is tolerated by the animal. Doses above this level are overtly toxic or fatal to the animal.

An oral formulation of an anti-viral composition of the invention was prepared according to the following procedure. A 0.75% solution of methyl cellulose was prepared by adding 7.5 g of methyl cellulose to 1 liter of boiling water. The solution was allowed to reach room temperature, and was brought to 4° C. while being stirred continuously until the methyl cellulose was completely dissolved. An appropriate quantity of the compound of the invention was added to one half the desired final volume of 0.75% methyl cellulose solution in a ground glass homogenizer. A uniform suspension of the compound and methyl cellulose solution was made by homogenization. The homogenized suspension was transferred to a separate container. The homogenizer was rinsed with the second one half of the 0.75% methyl cellulose solution. The rinse was combined with the homogenized suspension, and the combined solution was mixed by vortexing to ensure complete homogeneity of the solution. The suspension was stored at 4° C.

To assess the safety of compounds of the invention, the methyl cellulose formulations of compounds of the invention were administered to laboratory mice. A single dose of each compound in a 0.5 mL volume was administered by oral gavage to groups of test animals, each consisting of five female Swiss Webster mice 8 to 9 weeks of age and weighing 25 to 30 g. The MTD was determined by administering increasing doses of compound and assessing animal survival over a 7 day period. Table 5 shows the results from this experiment, which involved three compounds of the present invention.

TABLE 5

| Group | Compound | Dose (mg/kg) | # Survivors (alive at Day 7) | MTD (mg/kg) |
| --- | --- | --- | --- | --- |
| 1 | None | 0 | 5/5 | — |
| 2 | Example 1 | 21 | 5/5 | |
| 3 | | 71 | 5/5 | |
| 4 | | 214 | 5/5 | |
| 5 | | 710 | 5/5 | $\geq 710$ |
| 6 | Example 7 | 21 | 5/5 | |
| 7 | | 71 | 5/5 | |
| 8 | | 214 | 5/5 | |
| 9 | | 710 | 5/5 | $\geq 710$ |
| 10 | Example 9 | 21 | 5/5 | |
| 11 | | 71 | 5/5 | |
| 12 | | 214 | 5/5 | 214 |
| 13 | | 710 | 0/5 | |

The results given in Table 5 indicate that the compounds of Examples 1 and 7 were safe at all doses tested, as those compounds had MTD's of greater than or equal to the highest dose tested. The MTD for the compound prepared in Example 9 was determined to be 214 mg/kg.

EXAMPLE 33

Bioavailability Studies

Useful inhibitor compounds must be bioavailable, which means that upon administration of such inhibitors to living beings, the inhibitors must be present and available in bodily fluids or tissues where virus replication occurs. Typically, determination of compound levels in the plasma or serum of living beings to which the compound has been administered provides a measure of the compound's bioavailability.

To assess the bioavailability of compounds of the invention, methyl cellulose formulations of compounds, prepared as in Example 32, above, were administered to laboratory mice as described above at two doses; 21 mg/kg and 214 mg/kg. At 30 minutes and 90 minutes after compound administration by oral gavage, groups of five mice were exsanguinated by cardiac puncture, their blood was pooled, and serum was prepared.

The level of compound in these sera was then determined by biological evaluation of the antiviral potency of the sera as follows. A concentration curve standard for each test compound was established by adding a known amount of the compounds under test to normal mouse serum. Serial dilutions of these spiked reference sera, as well as the sera from the mice administered the test compounds, were prepared in DMEM supplemented with 2% horse serum. These dilutions were added to the medium of BVDV-infected MDBK cells plated on 96-well plates as described above in Example 29. The plates were then incubated at 37° C. in a humidified atmosphere containing 2.5% carbon dioxide for 36–40 hours. At the end of the incubation period, the cell monolayers were fixed with glutaraldehyde, and the cells were stained with crystal violet as described in Example 29. The optical density of the wells was measured at 570 nm.

The concentration of the reference compounds that protected 50% of the cell monolayer from virus-induced cytopathic effect was determined. Those values were used to estimate the concentration of compound in the serum of orally-dosed mice. For example, the $IC_{50}$ value for the compound prepared in Example 1 evaluated with the spiked mouse reference serum was determined to be 0.0035 uM. This $IC_{50}$ value was achieved with serum derived from mice 30 minutes after being administered a 214 mg/kg dose of the compound prepared in Example 1 which had been diluted 314-fold. By multiplying the reference serum $IC_{50}$ value by the test serum dilution factor, the compound concentration in the test serum was determined to be 1.1 $\mu$M.

TABLE 6

Mouse Serum Concentration of Triazinoindoles After Single Oral Dose

| Compound | Dose (Mg/Kg) | Concentration Of Drug ($\mu$M) Measured In Serum Post Drug Administration | |
| --- | --- | --- | --- |
| | | 30 Min. | 90 Min. |
| Example 1 | | | |
| | 21 | 0.1 | 0.07 |
| | 214 | 1.1 | 0.6 |
| Example 7 | | | |
| | 21 | <1.5 | <1.5 |
| | 214 | 46.0 | 36.2 |
| Example 9 | | | |
| | 21 | 0.7 | <0.2 |
| | 214 | 19.6 | 8.5 |

As shown in Table 6, significant levels of each of the three compounds tested were found in the mouse sera. Based on the $IC_{50}$ values for these compounds determined in cell culture (0.006 uM for the compound prepared in Example 1, 0.06 uM for the compound prepared in Example 7, and 0.03 uM for the compound prepared in Example 9, levels of all three compounds well in excess of that exhibiting in vitro effectiveness were achieved in sera after oral administration of the compounds to mice. These results indicate considerable bioavailability of the compounds of the invention. Combined with the in vitro potency, selectivity and safety of the compounds demonstrated in Examples 29–32, the bioavailability data are predictive of the antiviral therapeutic effectiveness in recipients of the compounds of the invention.

Although the present invention has been described and exemplified in terms of certain preferred embodiments, other embodiments will be apparent to those skilled in the art. For example, further testing may show the usefulness of the compounds of the invention in the prevention and treatment of flavivirus and hepacivirus infections in both animals and humans. The invention is, therefore, not limited to the particular embodiments described and exemplified, but is capable of modification or variation without departing from the spirit of the invention, the full scope of which is delineated by the appended claims.

What is claimed is:

1. A compound having the formula:

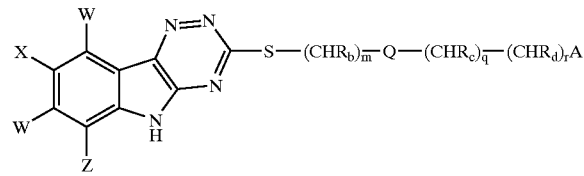

wherein A represents a substituent selected from the group consisting of:
(a) $NR_1R_2$ wherein $R_1$ is a radical selected from the group consisting of H, a straight or branched chain alkyl group ($C_1$–$C_6$), a substituted or unsubstituted aryl ($C_6$–$C_{15}$) group, a substituted or unsubstituted aralkyl ($C_7$–$C_{15}$) group in which the alkyl group is $C_1$–$C_6$, an alkoxy group ($C_1$–$C_6$), an acyl group ($C_1$–$C_7$), a substituted or unsubstituted carbalkoxy group ($C_1$–$C_8$ alkoxy), $R_2$ is a radical selected from the group consisting of a substituted or unsubstituted aryl ($C_6$–$C_{15}$) group, a substituted or unsubstituted aralkyl ($C_7$–$C_{15}$) group in which the alkyl group is $C_1$–$C_6$, an alkoxy group ($C_1$–$C_6$), an acyl group ($C_1$–$C_7$) a substituted or unsubstituted carbalkoxy group ($C_1$–$C_8$ alkoxy), or $R_1$ and $R_2$, together with the nitrogen atom to which they are attached, represent a substituted or unsubstituted heterocyclic ring selected from the group consisting of benzopyridazine, indole, benzotriazole, hexamethyleneimine, imidazole, isoxazole, and phthalimide;
(b) a substituted or unsubstituted heterocyclic group selected from the group consisting of pyridine, benzimidazole, benzodioxane, benzofurazan, indole, benzothiophene, coumarin, furan, hexamethyleneimine, isoxazole, oxadiazole, piperazine, piperidine, pyridine, pyrimidine, pyrrolidine, quinoline, quinuclidine, tetrahydropyran and thiazole, the point of attachment of said substituted or unsubstituted heterocyclic group being at a carbon atom of the heterocyclic ring; and
(c) $OR_3$, wherein $R_3$ represents a radical selected from the group consisting of H, a straight or branched chain alkyl ($C_1$–$C_6$) group, a substituted or unsubstituted phenyl group, a substituted or unsubstituted phenylalkyl group wherein the alkyl group is $C_1$–$C_6$, or substituted or unsubstituted tetrahydropyran;
Q represents a linking moiety selected from the group consisting of —[(A')$_n$—(CO)]$_p$—, —S—, —(SO)—, —(SO$_2$)— or a valence bond, A' being —NR$_a$— or —O— and R$_a$ being H or alkyl ($C_1$–$C_6$); R$_b$, R$_c$ and $R_d$ independently represent H, alkyl ($C_1$–$C_4$), substituted or unsubstituted phenyl or COOR, R being hydrogen or alkyl ($C_1$–$C_6$); m is an integer from 0 to 6; n and p independently represent 0 or 1; and q and r are independently integers from 0 to 4; said phenyl, aryl, aralkyl, carbalkoxy and heterocyclic substituents and the W, X, Y and Z substituents being selected from the group consisting of H, alkyl ($C_1$–$C_6$), substituted or unsubstituted aryl ($C_6$–$C_{15}$), substituted or unsubstituted aralkyl ($C_7$–$C_{15}$), halogen, $CF_3$, CN, O-alkyl ($C_1$–$C_6$), acyloxy ($C_1$–$C_6$ acyl), S-alkyl ($C_1$–$C_6$), SO-alkyl ($C_1$–$C_6$), $SO_2$-alkyl ($C_1$–$C_6$), $NH_2SO_2$, $NO_2$, $NH_2$, NHR', NR'R", alkyl ($C_1$–$C_6$) COOR', alkyl ($C_1$–$C_6$) CONR'R", CONR'R",

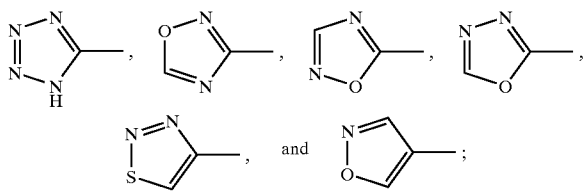

R' and R" being independently selected from the group consisting of hydrogen or alkyl ($C_1$–$C_6$), and the isomers or pharmaceutically acceptable salts of said compound.

2. A compound as claimed in claim 1, wherein A represents $NR_1R_2$.

3. A compound having the formula:

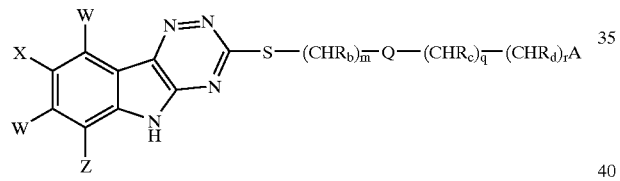

wherein A represents $OR_3$, and $R_3$ is a radical selected from the group consisting of H, a straight or branched chain alkyl ($C_1$–$C_6$) group, a substituted or unsubstituted phenyl group a substituted or unsubstituted phenylalkyl group wherein the alkyl group is $C_1$–$C_6$, or substituted or unsubstituted tetrahydropyran;

Q represents a linking moiety selected from the group consisting of —[(A')$_n$—(CO)]$_p$—, —S—, —(SO)—, —($SO_2$)— or a valence bond, A' being —$NR_a$— or —O— and $R_a$ being H or alkyl ($C_1$–$C_6$); $R_b$, $R_c$ and $R_d$ independently represent H, alkyl ($C_1$–$C_4$), substituted or unsubstituted phenyl or COOR, R being hydrogen or alkyl ($C_1$–$C_6$); m is an integer from 0 to 6; n and p independently represent 0 or 1; and q and r are independently integers from 0 to 4; said phenyl, and tetrahydropyran substituents and the W, X, Y and Z substituents being selected from the group consisting of H, alkyl ($C_1$–$C_6$), substituted or unsubstituted aryl ($C_6$–$C_{15}$), substituted or unsubstituted aralkyl ($C_7$–$C_{15}$), halogen, $CF_3$, CN, O-alkyl ($C_1$–$C_6$), acyloxy ($C_1$–$C_6$ acyl), S-alkyl ($C_1$–$C_6$), SO-alkyl ($C_1$–$C_6$), $SO_2$-alkyl ($C_1$–$C_6$), $NH_2SO_2$, $NO_2$, $NH_2$, NHR', NR'R", alkyl ($C_1$–$C_6$) COOR', COOR', alkyl ($C_1$–$C_6$) CONR'R", CONR'R",

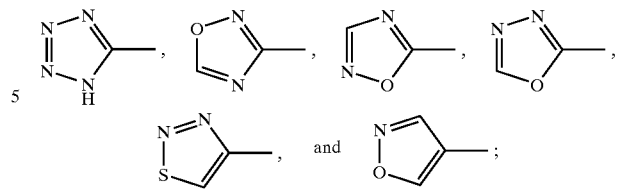

R' and R" being independently selected from the group consisting of hydrogen or alkyl ($C_1$–$C_6$), and the isomers or pharmaceutically acceptable salts of said compound.

4. A compound having the formula:

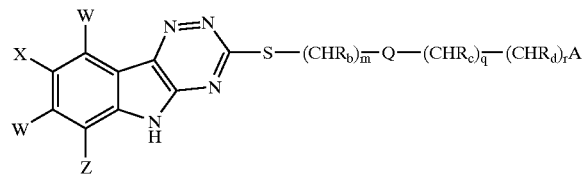

wherein A represents a substituted or unsubstituted heterocyclic group selected from the group consisting of pyridine, benzimidazole, benzodioxane, benzofurazan, indole, benzothiophene, coumarin, furan, hexamethyleneimine, isoxazole, oxadiazole, piperazine, piperidine, pyridine, pyrimidine, pyrrolidine, quinoline, quinuclidine, tetrahydropyran and thiazole, the point of attachment of said substituted or unsubstituted heterocyclic group being at a carbon atom of the heterocyclic ring; and (b) Q represents a linking moiety selected from the group consisting of —[(A')$_n$—(CO)]$_p$—, —S—, —(SO)—, —($SO_2$)— or a valence bond, A' being —$NR_a$— or —O— and $R_a$ being H or alkyl ($C_1$–$C_6$); $R_b$, $R_c$, and $R_d$ independently represent H, alkyl ($C_1$–$C_4$), substituted or unsubstituted phenyl or COOR, R being hydrogen or alkyl ($C_1$–$C_6$); m is an integer from 0 to 6; n and p independently represent 0 or 1; and q and r are independently integers from 0 to 4; said heterocyclic substituents and the W, X, Y and Z substituents being selected from the group consisting of H, alkyl ($C_1$–$C_6$), substituted or unsubstituted aryl ($C_6$–$C_{15}$), substituted or unsubstituted aralkyl ($C_7$–$C_{15}$), halogen, $CF_3$, CN, O-alkyl ($C_1$–$C_6$), acyloxy ($C_1$–$C_6$ acyl), S-alkyl ($C_1$–$C_6$), SO-alkyl ($C_1$–$C_6$), $SO_2$-alkyl ($C_1$–$C_6$), $NH_2SO_2$, $NO_2$, $NH_2$, NHR', NR'R", alkyl ($C_1$–$C_6$) COOR', COOR', alkyl ($C_1$–$C_6$) CONR'R", CONR'R",

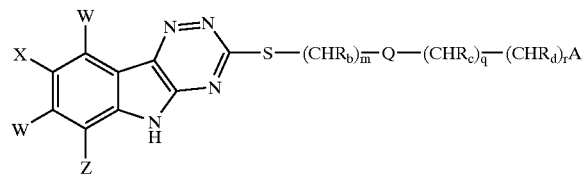

R' and R" being independently selected from the group consisting of hydrogen or alkyl ($C_1$–$C_6$), and the isomers or pharmaceutically acceptable salts of said compound.

5. A compound as claimed in claim 1, selected from the group consisting of 3-[(2-pyridylmethyl)thio]-5H-1,2,4-triazino[5,6-b]indole, 3-[4-((6,7-dimethoxy-2-oxo-2H-1-benzopyranyl)methyl)thiol-5H-1,2,4-triazino[5,6-b]indole, 3-[(2-(benzodioxanyl)methyl)thio]-5H-1,2,4-triazino[5,6-b]

indole, 3-[(4-(2,6-dichloropyridyl)methyl)thio]-5H-1,2,4-triazino[5,6-b]indole and 3-[4-(((2-tetrahydro-2H-pyranyl)oxy)butyl)thio]-5H-1,2,4-triazino[5,6-b]indole.

6. A compound as claimed in claim 1, selected from the groups consisting of 3-[(2-(1-hexamethyleneimino)ethyl)thio]-5H-1,2,4-triazino[5,6-b]indole, 3-[(2-(1-hexamethyleneimino)ethyl)thio]-8-methyl-5H-1,2,4-triazino{5,6-b)-indole, 3-[(2-(1-hexamethyleneimino)ethyl)thio]-8-bromo-5H-1,2,4triazino[5,6-b]-indole, and 3-[(2-(1-hexamethyleneimino)ethyl)thio)-8-fluoro-5H-1,2,4triazino[5,6-b]-indole.

7. A Pharmaceutical composition comprising a compound of claim 1 in admixture with a pharmaceutically acceptable carrier.

8. A pharmaceutical composition comprising a compound of claim 3 in admixture with a pharmaceutically acceptable carrier.

9. A pharmaceutical composition comprising a compound of claim 4 in admixture with a pharmaceutically acceptable carrier.

10. A pharmaceutical composition as claimed in claim 7 in the form of a solid comprising said compound and a pharmaceutically acceptable excipient.

11. A pharmaceutical composition as claimed in claim 7 in the form of a liquid comprising said compound and a pharmaceutically acceptable diluent.

12. A composition as claimed in claim 7 in dosage unit form comprising per unit about 0.1 to about 50 mg. of said compound.

13. A method of treating mammalian cells in culture that are susceptible to infection by, or infected or contaminated with a pestivirus, said method comprising administering to said cultures an effective amount of a compound according to claim 1.

14. A method for the in vitro treatment of biological material that is susceptible to infection by, or infected or contaminated with a pestivirus, said method comprising treating said material with an effective amount of a compound according to claim 1.

* * * * *